US00PP26151P2

(12) United States Plant Patent
Williams

(10) Patent No.: US PP26,151 P2
(45) Date of Patent: Nov. 24, 2015

(54) ***COLOCASIA* PLANT NAMED 'BLACK RIPPLE'**

(50) Latin Name: ***Colocasia* hybrid**
Varietal Denomination: Black Ripple

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 85 days.

(21) Appl. No.: 13/987,197

(22) Filed: Jul. 10, 2013

(51) Int. Cl.
*A01H 5/00* (2006.01)

(52) U.S. Cl.
USPC ..... Plt./373

(58) Field of Classification Search
USPC ..... Plt./373
CPC ..... A01H 5/12; A01H 5/00
See application file for complete search history.

(56) References Cited

PUBLICATIONS

Plants Nouveau, retrieved from Google Search on Nov. 15, 2014.*

* cited by examiner

*Primary Examiner* — Keith O. Robinson
(74) *Attorney, Agent, or Firm* — Penny J. Aguirre

(57) ABSTRACT

A new cultivar of *Colocasia* plant named 'Black Ripple', that is characterized by its leaves that are very dark black-purple in color with a surface that is corrugated (puckered), iridescent and shiny, its dwarf and compact plant habit, its petioles that are deep purple in color, its clump forming growth habit, and its vigorous growth habit.

2 Drawing Sheets

Botanical classification: *Colocasia* hybrid.
Cultivar designation: 'Black Ripple'.

BACKGROUND OF THE INVENTION

The present invention, *Colocasia* 'Black Ripple', relates to a new and distinct interspecific hybrid of *Colocasia*, hereinafter referred to by its cultivar name, 'Black Ripple'. 'Black Ripple' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Black Ripple' arose from a cross made in July of 2009 between unnamed plants of a *Colocasia* of hybrid origin from the Inventor's breeding programs as the female and male parents. 'Black Ripple' was selected as a single unique plant in June of 2011 from amongst the seedlings derived from the above cross.

Asexual propagation of the new cultivar was first accomplished by in vitro propagation under the direction of the Inventor in Eustis, Fla. in May of 2012. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Black Ripple' as a new and unique cultivar of *Colocasia*.

1. 'Black Ripple' exhibits leaves that are very dark black-purple in color.
2. 'Black Ripple' exhibits a dwarf and compact plant habit; reaching 0.9 to 1.2 m (3 to 4 ft) in height.
3. 'Black Ripple' exhibits leaves with a surface that is corrugated (puckered), iridescent and shiny.
4. 'Black Ripple' exhibits petioles that are deep purple in color.
5. 'Black Ripple' exhibits a clump forming growth habit (lacking stolons).
6. 'Black Ripple' exhibits a vigorous growth habit.

The female parent of 'Black Ripple', an unnamed plant of *Colocasia* of hybrid origin, differs from 'Black Ripple' in being taller in height, in having leaves that are dark green in color with a matte surface, and in producing stolons. The male parent of 'Black Ripple', an unnamed plant of *Colocasia* of hybrid origin, differs from 'Black Ripple' in being taller in height, and in having leaves that are brown-black in color with a non corrugated appearance. 'Black Ripple' can be most closely compared to *Colocasia* cultivars 'Black Magic' (not patented) and 'Illustris' (not patented). Both are similar to 'Black Ripple' in having large leaves that have dark coloration. 'Black Magic' differs from 'Black Ripple' in being shorter in height, and in having leaves that are grayer in color, non corrugated, and exhibit a matte surface. 'Illustris' differs from 'Black Ripple' in being shorter in height and in having leaves that are non corrugated with a matte finish and green suffused with purple in color with distinct green veins.

BRIEF DESCRIPTION OF THE DRAWINGS

The accompanying colored photographs illustrate the overall appearance and distinct characteristics of the new *Colocasia*, 'Black Ripple'. The photographs were taken of plants about 2 years in age as grown outdoors under 6 mm poly and natural lighting in Louisville, Ky. and planted in a trial garden.

Figure 1:
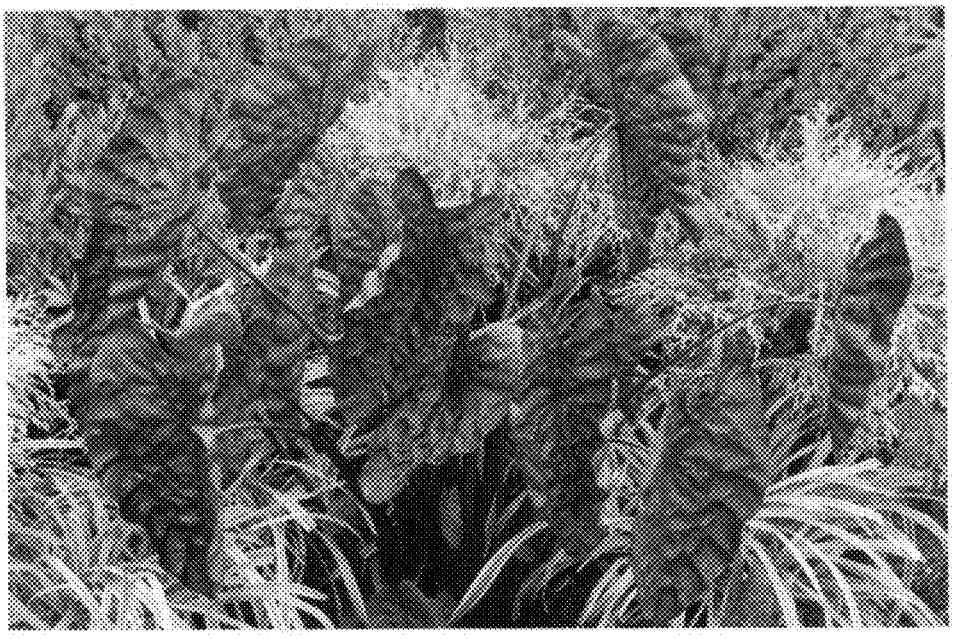
FIG. 1 provides an overall view of the foliage, petioles and plant habit of 'Black Ripple'.
Figure 2:
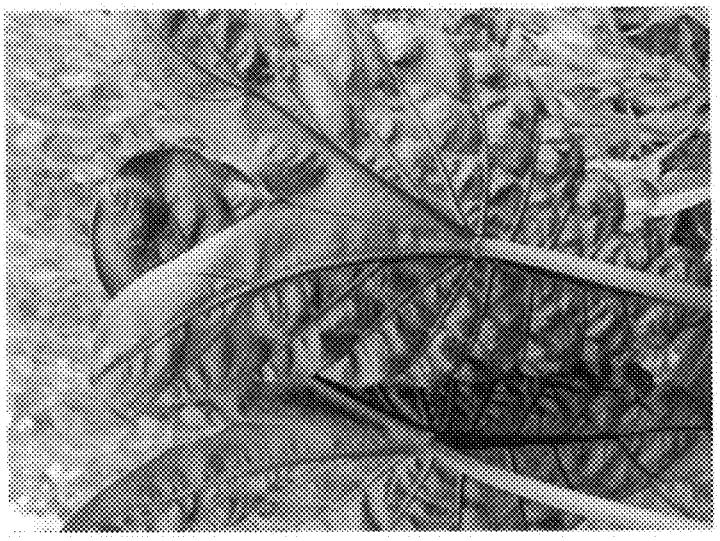

The photograph in FIG. 2 provides a close-up view of the lower surface of a leaf of 'Black Ripple' in winter.

Figure 3:
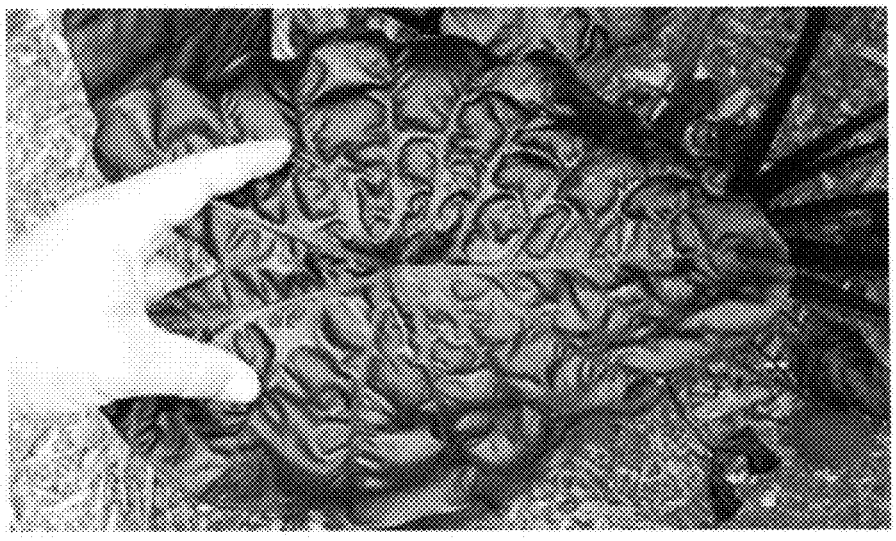

The photograph in FIG. 3 provides a close-up view of the upper surface of a mature leaf of 'Black Ripple'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of three year-old plants of the new cultivar as grown outdoors in a garden under full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid summer until frost in Kentucky.

*Plant type*.—Tropical perennial herb, stemless.

*Plant habit*.—Dwarf, compact, clump forming.

*Height and spread*.—Reaches 0.9 to 1.2 m (3 to 4 ft) in height and about 0.9 m (3 ft) in spread.

*Cold hardiness*.—At least to U.S.D.A. Zone 7.

*Diseases and pests*.—No particular resistance or susceptibility has been shown to diseases or pests.

*Roots*.—Fleshy, produced in a compact mass, no stolons produced, 182B in color with growing tips 161D.

*Propagation type*.—In vitro propagation is preferred.

*Root development*.—Tissue culture plugs will fully root in a one-gallon container in 2 to 3 months with sufficient heat and sun.

*Corm*.—Nearly round in shape, an average of 3.5 cm in diameter, N199D in color.

*Growth rate*.—Vigorous.

*Stem description*.—Stemless.

Foliage description:

*Leaf shape*.—Ovate.

*Leaf division*.—Single.

*Leaf base*.—Cordate.

*Leaf apex*.—Acute, slight cuspidate tip.

*Leaf venation*.—Pinnate, raised on upper and lower surface, color: upper surface; matches leaf coloration, lower surface; N77A.

*Leaf margins*.—Undulate.

*Leaf attachment*.—Petiolate.

*Leaf arrangement*.—Alternate.

*Leaf number*.—An average of 16 leaves on a plant 3 years in age as grown in the garden.

*Leaf surface* (*texture*).—Upper surface and lower surface; corrugated (puckered) and shiny, upper surface has an iridescent appearance as well.

*Leaf orientation*.—Held outward (perpendicular to petiole).

*Leaf color*.—Young foliage: upper surface; N186A, lower surface; a blend of N187A, N187B, and 147A, mature foliage upper surface; a blend of N187A and 202A and becoming almost solid 202A in winter, mature lower surface; a blend of N77A and N77B.

*Leaf size*.—Up to 61 cm in length and 45.7 cm in width.

*Leaf sinus*.—An average of 8.5 cm in depth on a mature leaf.

*Petioles*.—Held erect to about a 45° angle (gently cascading on upper portion), about 91.4 cm in length and 1.3 cm in distal diameter and 5 cm in proximal diameter, glabrous and glossy surface, N77C in color, the basal sheath portion is narrowly triangular in shape, N77C in color on both surfaces, 5 cm in diameter and 9 cm in length, glabrous and glossy surface.

Inflorescence description:

*Inflorescence type*.—Spadix surrounded by a spathe.

*Inflorescence size*.—Average of 35 cm in length and 3 cm in diameter.

*Inflorescence bud*.—Linear to slightly narrow oblanceolate in shape, an average of 17 in length and 1.5 cm in width, 186B in color.

*Flower fragrance*.—Slight banana smell.

*Lastingness of inflorescence*.—Inflorescence blooms intermittently during the bloom period, individual flowers last about 2 to 3 weeks.

*Inflorescence/flower quantity*.—Intermittent throughout the bloom season, an average of 250 female flowers per spadix and 1 male flower.

*Spathe*.—Hooded, bract, subtending spadix, elliptic in shape, entire margin, acute apex, coriaceous surface, 14 cm in length and 3 cm in width, lasts 5 to 7 days, color: when opening and fully open on inner surface; N186C to N186D and outer rear surface; a blend of N186A to N186B and N187A, fading to 202A.

*Spadix*.—Male portion above female zone, upright cylindrical shape (phallus-like), apex narrowly pointed, about 9 mm in diameter (not including ovary) and 8 cm in length, male zone; 6 cm in diameter and 4.4 cm in length, color immature and mature N186A to N186B, female zone; 9.5 mm in diameter and 3 cm in length, color immature and mature a mix of N79C, 155C, N187A.

*Peduncle*.—Emerges from base of plant, up to 21 cm in length and 9 mm cm in diameter, held upright, strong, a blend of N186A to N186B and N187A in color, glaucescent surface.

Reproductive organs:

*Gynoecium*.—Stigmas are N79C in color, ovary is globose in shape and N155D in color.

*Androcoecium*.—Undeveloped.

*Fruit and seed*.—Sterile.

It is claimed:

1. A new and distinct cultivar of *Colocasia* plant named 'Black Ripple' as herein illustrated and described.

* * * * *